United States Patent [19]

Bernhardt et al.

[11] Patent Number: 4,788,054

[45] Date of Patent: Nov. 29, 1988

[54] N-PHENYLPHTHALISOMIDES AS ULTRAVIOLET RADIATION ABSORBERS

[75] Inventors: Randal J. Bernhardt, Mundelein; William J. Ferrell, Des Plaines, both of Ill.

[73] Assignee: Stepan Company, Northfield, Ill.

[21] Appl. No.: 884,350

[22] Filed: Jul. 11, 1986

[51] Int. Cl.[4] .......................... A61K 7/06; A61K 7/42; A61K 9/10; A61K 9/12
[52] U.S. Cl. ............................. 424/59; 424/DIG. 10; 424/47; 424/60; 424/70; 424/78; 424/80; 424/81; 514/937; 514/938
[58] Field of Search ........................................... 424/59

[56] References Cited

U.S. PATENT DOCUMENTS 4,333,920  6/1982  Conner .................................. 424/59

FOREIGN PATENT DOCUMENTS 1293312  10/1972  United Kingdom .................. 424/47

Primary Examiner—Dale R. Ore
Attorney, Agent, or Firm—Andrew F. Zikas

[57] ABSTRACT

A class of N-phenylphthalisoimides is provided which demonstrate broad spectrum ultraviolet radiation absorbing capacities for protecting various substrate materials including plastics, fibers, human skin, hair and the like, from the effects of such radiation. Such compounds can be incorporated either into coating compositions for such substrates or into the substrates themselves, depending upon the substrate materials, use conditions, etc.

19 Claims, No Drawings

N-PHENYLPHTHALISOMIDES AS ULTRAVIOLET RADIATION ABSORBERS

BACKGROUND OF THE INVENTION

1. Field of the Invention

This invention lies in the field of ultraviolet radiation absorbers and particularly involves the use of certain pthalisoimides as substrate protectants for ultraviolet radiation.

2. Prior Art

It is known that light, in particular, ultraviolet (UV) radiation, causes the breakdown of various manufactured substances, such as synthetic polymers, natural fibers, and the like. UV radiation also damages human skin and hair. UV radiation in wavelengths ranging between about 290 and 320 nanometers (nm), is sometimes called UV-B radiation, and that between about 320 and 400 nm is sometimes called UV-A radiation.

UV-B radiation from the sun reportedly causes almost all of the photobiological skin reactions, including erythema, edema, blistering, and skin cancer. The longer UV-A rays produce minor photobiological reactions, such as immediate tanning and immediate transient erythema responses. Together, UV-A and UV-B radiation are responsible for the majority of photoinjuries to the skin.

Therefore, broad spectrum ultraviolet radiation absorbers are needed to protect both manufactured products (such as polymers, fabrics, and the like) and natural products (such as human skin and hair), from the damaging effects of UV radiation. For manufactured products, this can be accomplished by either coating the product, or incorporating into the product (especially surface regions), a UV absorber or mixture of UV absorbers. Broad formulation compatibility is desirable. For protecting natural surfaces, sunscreen compositions that incorporate UV absorbers or mixtures of UV absorbers are applied topically, and UV absorbers so incorporated must additionally be nontoxic to mammals (including man). UV absorbers which are relatively inexpensive to produce are desirable.

Broad spectrum screening of ultraviolet radiation in sunscreen compositions is generally accomplished by two techniques. In one technique, a UV-B absorber is admixed with a UV-A absorber and the mix is blended into a suitable cosmetic carrier. This technique is usually expensive because of the high cost of each absorber.

In the second technique, a single compound that absorbs both UV-A and UV-B radiation is blended into a suitable cosmetic carrier. An example of a prior art compound employed in practicing this second technique is a benzalphthalide of the type taught in U.S. Pat. No. 4,333,920, issued June 8, 1982 which discloses such benzalphthalides to be effective as broad spectrum sunscreens that absorb UV radiation over the range from about 290 nm to 350 nm. However, benzalphthalides suffer from the problems associated with other prior art broad spectrum UV absorbers or screens, which are: high manufacturing costs, low product yield, and, therefore, high cost of final product.

A practical broad spectrum UV absorber should protect manufactured products and/or human skin and hair from the harmful effects of the UV-A and UV-B radiation, and also be resistant to oxidation and photodegradation under all storage and application conditions. It is desirable that the UV absorber be economical to produce. Also, a broad spectrum UV absorber for cosmetic use should be substantially oil-miscible or capable of forming a non-granular smooth suspension in conventional cosmetic oil carriers suitable for use in sunscreen compositions. Further, such broad spectrum UV absorber should be effective, substantially nontoxic, and cosmetically acceptable under normal use conditions. Still further, such a UV absorber for use in protecting manufactured products should be compatible with the other agents commonly used in such products. The art needs new and improved broad spectrum UV absorbers having a combination of such properties.

BRIEF SUMMARY OF THE INVENTION

This invention relates to the discovery that certain phthalisoimides, namely N-phenylphthalisoimide and substituted N-phenylphthalisoimides, are very effective broad spectrum UV radiation absorbers, which can be used in compositions for protecting various substrate materials, including plastics, fibers, human skin, hair, and the like from the deleterious effects of artificial and natural radiation. Such phthalisoimides can be either applied as a coating or incorporated directly into a substrate, depending upon conditions and the materials involved.

In one aspect, the present invention relates to a method for protecting substrates, a present preference being mammalian skin or hair, from the effects of ultraviolet radiation by first incorporating at least one N-phenylphthalisoimide compound of the class hereinbelow described into a coating composition and then applying such coating composition to such substrate. This aspect of the invention further relates to the novel coating compositions containing such N-phenylphthalisoimides which compositions are useful in the practice of such method.

One class of such coating compositions comprises sunscreen compositions which absorb UV radiation when applied topically to living skin or hair.

Another class of such coating compositions comprises initially liquid compositions which, when coated upon an inanimate substrate, dry to produce a relatively solvent insoluble, relatively thermoset polymeric protective coating which absorbs UV radiation.

The substrates involved in this aspect of the invention further includes articles of manufacture which bear such a UV absorbing polymeric coating. Such coatings can be transparent or translucent, and preferred substrates for such coatings include window glass, lenses, and the like as well as transparent and translucent UV-sensitive plastic films and sheets, fabrics which have been dyed with UV-sensitive dyes and the like.

In another aspect, the present invention relates to a method for protecting a thermoplastic or thermosetable resin from the effects of ultraviolet radiation by incorporating into such a resin, when in a moldable form, at least one N-phenylphthalisoimide compound of the class hereinbelow described, and then thereafter conventionally molding such resulting moldable resin formulations into an article of manufacture. This aspect of the invention further relates to the N-phenylphthalisoimide containing moldable resin formulations which are useful in the practice of such method.

One class of such moldable resin formulations comprises thermoplastic moldable resins in particulate form.

Another class of such moldable (including castable) resin formulations comprises thermosetable resins in particulate form, such as a molding powder, a liquid, or the like.

This aspect of the invention further includes ultraviolet radiation absorbing molded plastic articles of manufacture which are produced from such resin formulations. Examples of such articles include lenses for sunglasses and other optical goods, transparent and translucent molded elements for electric light fixtures, plastic sheeting (including film), window and automotive glass, and the like.

A principal object of the present invention is to provide improved methods and compositions, and articles of manufacture for achieving ultraviolet radiation absorption for purposes of protecting skin and hair from the effects of ultraviolet radiation exposure.

Another object is to provide novel methods, compositions and articles of manufacture for protecting ultraviolet radiation sensitive materials from such radiation by using at least one member of a class of certain N-phenylphthalisoimides as more fully hereinbelow characterized.

Another object is to utilize as broad spectrum UV absorbers, which are effective with both UV-A and UV-B radiation, one or more members of the indicated class of N-phenylphthalisoimides.

Another object is to provide a class of broad spectrum UV absorbers which are effective, substantially nontoxic, cosmetically acceptable, and substantially oil-miscible or capable of forming nongranular smooth suspensions in cosmetic oil carriers, and which are thus suitable for use in sunscreen compositions.

Another object is to provide coating compositions for applying polymeric coatings to substrates, which coatings absorb incident UV radiation and which coatings incorporate at least one N-phenylphthalisoimide.

Another object is to provide improved methods for achieving UV absorption using N-phenylphthalisoimides, which are broad spectrum UV absorbers.

Another object is to provide improved compositions which achieve UV absorption through incorporation thereunto of broad spectrum UV absorbing N-phenylphthalisoimides.

Another object is to provide improved articles of manufacture which achieve UV absorption through association and/or incorporation onto or into such articles of broad spectrum UV absorbing N-phenylphthalisoimides.

Another object is to provide improved sunscreen compositions incorporating broad spectrum UV absorbing N-phenylphthalisoimides which are substantially nontoxic, substantially non-irritating to skin, and which are dispersible or dissolvable in conventional cosmetic oils.

Other and further objects, aims, purposes, features, advantages, embodiments, and the like will become apparent to those skilled in the art from the teachings of the present specification and claims.

DETAILED DESCRIPTION

Active Agents

The class of UV radiation absorbing phthalisoimide compounds employed in this present invention comprise N-phenylphthalisoimides and substituted N-phenylphthalisoimides having the generic formula:

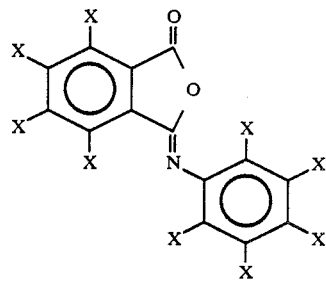

wherein:

each X is independently selected from the group of radicals consisting of hydrogen, —OR, —NR$_1$R$_2$, —Cl, —Br, —I, —NO$_2$, —C(O)OR, and hydrocarbyl, R is selected from the group consisting of alkyl radicals and alkenyl radicals containing less than 11 carbon atoms each, and R$_1$ and R$_2$ are each independently selected from the group of radicals consisting of hydrogen, alkyl radicals containing less than 11 carbon atoms each, and alkenyl radicals containing less than 11 carbon atoms each.

The term "hydrocarbyl" as used herein has reference to any carbon and hydrogen containing radical, including aliphatic, aryl, aralkyl, and alkaryl, each containing of from 1 to about 10 carbon atoms.

Utility

The compounds of formula (1) are useful as ultraviolet light absorbers. The compounds are believed to be substantially nonreactive with polymers including proteins, resins, common organic solvents, oils, and the like and hence such compounds can be readily and conveniently formulated therewith.

For example, thermoformable and thermosettable organic polymeric compositions incorporating formula (1) compounds are preparable which compositions and articles made therefrom are resistant to UV radiation degradation, and the like. Thus, fibers, various molded plastic bodies and the like can be prepared which have excellent UV screening and absorption properties.

For another example, formula (1) compounds can be formulated to make substrate surface coatings, resin blends, sunscreen compositions, and the like. Particularly when sunscreen compositions are involved, it is desirable to employ in substrate coating compositions compounds of formula (1) which are light colored and which are substantially nontoxic and nonirritating to skin, especially human skin. The compounds of formula (1) are believed to be generally substantially inert towards common solvents and vehicles, adjuvants, and fluid carriers, and the like, including low molecular weight inert organic compounds, such as hydrocarbons, ketones, aldehydes, ethers, esters, and the like which are commonly used as solvents and carriers, and also including higher molecular weight compounds which are oils, viscous liquids, pastes or even solids at ambient temperatures.

As those skilled in the art will readily appreciate, the particular requirements and preferences associated with individual end use applications influence which particular formula (1) compound is used in any given application situation.

The ultraviolet absorbance of a formula (1) compound or mixture of formula (1) compounds is conveniently measured by its absorbativity of "K" value. A K value is determined by dividing the absorbance of UV radiation in a radiation transmission medium by the concentration of the formula (1) compound present at maximum lambda ( ) value for each compound in such medium expressed in grams per liter. The higher the K value, the greater the UV absorbance, and therefore, the lower the amount of UV absorber needed in a formulation to obtain a specified absorbance. High K values are particularly desirable in sunscreen formulations as those skilled in the art appreciate.

The ultraviolet absorbance characteristics of formula (1) compounds characteristically vary from one such compound to another. The exact UV absorbance of a given formula (1) compound, and the changes in UV absorbance which occur from one compound to another, is not presently predictable based upon presently available information.

Compounds of formula (1) which display UV radiation absorbance both in the UV-A radiation wavelength region and the UV-B radiation wavelength region (sometimes are termed broad band absorbers herein) and are presently preferred for use in the compositions and methods of this invention, and particularly for use in sunscreen compositions.

Preparation

The N-phenylphthalisoimides of formula (1) can be prepared by any convenient procedure. For example, they can preferably be prepared from the corresponding N-phenylphthalamic acids and an appropriate dehydrating agent (See Sauers, C. K. et al., J. Amer. Chem. Soc. Vol. 94, No. 23, P.8156–63, 1972).

A procedure published by Cotter, J. C., et al., Org. Chem., Vol. 26, p. 10–15, 1960, teaches that isomaleimides are prepared by the dehydration of the corresponding maleamic acids with trifluoroacetic anhydride and triethylamine (TEA). When this method is applied to phthalamic acids, it is found that yields greater than 90% are sometimes obtainable (See Example 1 below). Other dehydrating agent combinations that can be used with phthalamic acids include ethylchloroformate and TEA, acetyl chloride and TEA, and also dicyclohexylcarbodiimide.

A mixed composition of N-phenylphthalisoimide isomers of formula (1) is obtained through the reaction of a substituted phthalic anhydride and a substituted aniline derivative. For use as UV absorbers in accordance with this invention, these isomers need not be separated, but can be used as a single starting composition. For example, a composition synthesized from 4-methylphthalic anhydride and 4-methoxyaniline comprises a mixture of N-4-methoxyhenyl-4-methylphthalisoimide and N-4-methoxyphenyl-6-methylphthalisoimide.

Presently preferred phthalamic acids suitable for use in synthesizing formula (1) compounds using the dehydration preparation procedure above referenced include: N-4-chlorophenylphthalamic acid, N-3,4-dichlorophenylphthalamic acid, N-4-methylphenylphthalamic acid, N-2-methoxyphenylphthalamic acid, 4-methoxyphenylphthalamic acid, N-4-methoxyphenyl-4-methylphthalamic acid, and N-phenylphthalamic acid.

Some compounds of formula (1) characteristically and advantageously can be prepared in high yields from relatively low cost, commercially available starting materials, such as, for example, phthalic anhydride and aniline.

Sunscreen Compositions

One presently preferred class of product compositions of the present invention comprises sunscreen compositions. Sunscreen compositions are formulated for application to mammalian skin, especially human skin, with the principal object being to reduce the level of ultraviolet radiation (from sunlight) effectively reaching the skin as compared to the level of such radiation which would otherwise reach the (untreated) skin at the same level of such radiation.

Presently preferred formula (1) compounds for use in sunscreen compositions are those wherein X is selected from the group consisting of —OR, —Cl, —C(O)OR, and hydrocarbyl, and R, $R_1$ and $R_2$ have their respective above defined meanings.

In sunscreen compositions, it is presently preferred to employ formula (1) compounds which absorb radiation both in the UV-A spectral band and in the UV-B spectral band.

Examples of presently particularly preferred embodiments of formula (1) compounds for use in sunscreen compositions include: N-4-chlorophenylphthalisoimide, N-3,4-dichorophenylphthalisomide, N-4-methoxyphenyl-4-methylphthalisoimide, N-phenylphthalisoimide, and the like.

Certain compounds of formula (1) are presently believed not to be desirable for use in sunscreen compositions of the present invention. For example, formula (1) compounds wherein X is nitro are generally not usable as broad spectrum ultraviolet light absorbers in sunscreen compositions because such compounds appear to absorb UV radiation mainly only around 400 nm. For another example, formula (1) compounds wherein X is amino ($NR_1R_2$) appear to be generally so highly colored as to be undesirable for use in sunscreen compositions unless suitable dyes are utilized. In those compounds of formula (1) wherein there is more than one single X substituent, the presence of a single such nitro or amino group among the X substituents indicates typically that the use of such resulting compound as a UV absorber in sunscreen compositions is undesirable.

Sunscreen compositions of this invention typically comprise at least one formula (1) compound dispersed and (including dissolved) in a cosmetic oil. Typically, from about 0.05 to 15 parts by weight of formula (1) compound are employed per each 100 parts by weight of such cosmetic oil, although larger and smaller quantities of such formula (1) compound(s) may be employed if desired in a given sunscreen composition without departing from the spirit and scope of the present invention. When in a dispersed (and non-dissolved) form, the formula (1) compounds are preferably in particle sizes which are less than about 500 millimicrons in average diameter and more preferably less than about 150 millimicrons in average diameter. A present preference is to employ from about 1.0 to 10 parts by weight of the above indicated preferred formula (1) compound(s) per each 100 parts by weight of such cosmetic oil with the formula (1) materials being preferably substantially completely dissolved in such oil.

For purposes of the present invention, the term "cosmetic oil" is used in its generally conventional sense to refer to a substantially chemically inert, substantially non-toxic, substantially topically non-irritating non-aqueous fluid material which is relatively non-volatile at ambient conditions. In general, any conventional cosmetic oil appears to be suitable for use in sunscreen compositions of the present invention.

Examples of classes of suitable such oils include:

(a) esters of fatty acids with at least one hydroxyl group containing compound 1 mono- di- and trialkanols each containing less than 7 carbon atoms per molecule, such as mixed glycerides, such vegetable oils, isopropyl palmitate, isopropylmyristate;

(b) petroleum derived hydrocarbon oils, (c) silicone oils, and the like.

Typical cosmetic oils, and related additives usable as vehicles or solvents in sunscreening compositions include:

almond, apricot kernel, avocado, castor, citrus seed, coconut cacao butter (also known as oil of theobroma), corn, cottonseed, egg, hydrogenated (various), jojoba oil lanolin (oil), linseed, mink, olive, palm, peach kernel, peanut (arachis), rapeseed, safflower, sesame, shark, soybean, turtle, whale, and wheat germ.

Additional types of cosmetic oils or other usable vehicles include:

mineral oils, isopropyl palmitate, Red Vet Pet, pharmaceutical grades of synthetic oils derived from natural fatty products (such as those available from Drew Chemical Corp. under the name Neobee M-5), Myvacet, dimethyl phthalate, liquid parrafin, silicones, oleyl alcohols, stabilized castor oil, stabilized castor oil combined with either polyethylene glycol 400 dilaurate, or triethanolamine aleate, liquid paraffin combined with stabilized castor oil, stearic acid, wool alcohol, cetyl alcohol, Polawax (a polyoxyethylene ester of sorbitan), glycerin, sodium citrate, silicon fluid such as MS200, perfume oil, water, N,N-Diethyltoluamide, glyceryl monostearate (non self-emulsifying), Polychol 5 (an ethoxylated lanolin alcohol preparation), butylated hydroxytoluene, hydroxyethyl cellulose (q.v.) and carboxymethylcellulose (q.v.) (such as available through Union Carbide under the name Cellosize QP 15000) triethanolamines, light amber petrolatum, calcium stearate, kaolin, Croda liquid base, water-soluble vinyl polymers (such as available through B. F. Goodrich Chemical Co. under the name Carbopol 940), polyol, Arlacel, Tween, glycerol monostearate, carbowaxes, methocels, ammonyxes, boric acid, ethoxylated derivatives of lanolin and lanolin components (such as available through American Cholesterol Products under the name of Solulan 16), isopropyl myristate, fatty acid esters, isopropyl palmitate, spermaceti, triethanolamine, hexadecyl alcohol, series of surface-active lanolin derivatives (such as available through American Cholesterol Products, Inc. under the name of Amerchol L-101), microcrystalline wax, beeswax, borax, lanogene, specially prepared acetylated lanolin (such as available through American Cholesterol Products, Inc. under the name Modulan), polyoxyethylene (POE) oleate/laurate, cerasynt MN, urea, gelamide, perhydrosqualene, Sunscreen Merida, Neo-Heliopan, isopropylan, metadelphene, vegetable oil, polyethoxylated high-molecular-weight amides (such as available through Armour Industrial Chemical Co. under the name Ethomid HT/15), series of emulsifiers and wetting agents which are polyoxyethylene ethers of higher aliphatic alcohols (such as available through ICI United States, Inc. under the name Brijs), ethohexadiol, prosolal S-9, series of lactate emolients (such as available through Van Dyk & Co., Inc. under the name Ceraphyl 140-A), ozokerite, ethoxylated lanolin forumulations such as Ritachol, fluorinated hydrocarbons (such as available through Allied Chemical Corp. under the name Genetron 11), and the like.

Sometimes relatively volatile organic solvents, such as ethanol, or the like are combinable into a sunscreen composition to enhance solubility of formula (1) compound(s).

One useful class or type of sunscreen compositions of this invention comprises:

(a) at least one of the above indicated preferred compounds of formula (1), and (b) cosmetic oil, such component (a) being dispersed in such component (b) at the rate of about 1.0 to 10 parts by weight of such component (a) per each 100 parts by weight of such component (b).

One presently preferred class or type of sunscreen compositions of this invention consists of emulsions of the type wherein water is the continuous phase and cosmetic oil is the discontinuous phase. The amount of water utilized can vary from one system to another, depending upon the formulator's objectives. One exemplary class of emulsion sunscreen compositions of this invention comprises on a 100 weight percent basis:

(a) from about 0.5 to 25 weight percent of at least one of the above indicated preferred compounds of formula (1) above, (b) from about 5 to 98 weight percent water, (c) from about 1 to 50 weight percent of cosmetic oil which oil, when emulsified in such a sunscreen composition, exists in the form of droplets whose average diameter is less than about 500 millimicrons, and (d) from 0 to about 15 weight percent of emulsifier, the amount of said emulsifier which is present in any given such sunscreen composition being at least sufficient to emulsify said cosmetic oil.

The many emulsifiers known to those skilled in the art of cosmetic emulsions are generally suitable for use in the emulsion compositions this invention. Preferably the emulsifier is chosen so as to produce a stable emulsified mixture of the cosmetic oil in the water which remains in existence even after a period of shelf storage.

Examples of suitable emulsifiers include long-chain fatty alcohols, glycerol fatty acid esters, polyethyleneglycol esters, anionic soaps, TEA stearate and the like. It is preferred to employ emulsifiers which can contribute to a desired tactile feeling such as is given by, or attributed to, cosmetic oils generally.

One presently more preferred class of sunscreen compositions of this invention comprises emulsions which have a viscosity which is appreciably greater than the viscosity of water. To some extent, emulsion viscosity is a matter of formulation preference, as when a pourable cream or thick lotion, as opposed to a thin lotion, is being formulated. While a cosmetic oil (and the emulsifier present) can themselves add to the viscosity of a given emulsion formulation, it is now preferred to incorporate a thickener (sometimes also called a viscosity modifier) into a composition in order to obtain a product sunscreen composition with increased viscosity. Examples of suitable thickeners include methylcellulose, hydroxyethylcellulose, hydrophilic polysaccharide gums (arabic, tragacanth, guar, karaya, etc.), gum rosins (gum benzoin, gum camphor, etc.), ester gums (semi-synthetic reaction products of rosin and a polyhydric alcohol), and the like. Typically, the amount of thickener utilized, if such is employed, can range from about 0.1 to 10 weight percent (based on 100 weight percent), although larger and smaller amounts can be employed if desired.

A sunscreen composition of the present invention can commonly and optionally include other substances, such as fragrances, humectants, preservatives, dyes, other types of ultraviolet radiation absorbers, and the like, all as known and understood by those skilled in the art of sunscreen compositions. Typically, when such other additives are present in a sunscreen composition of this invention, such additives are dispersed (and preferably dissolved) either in the cosmetic oil or in the water. Typically, the total combined amount of such additives is not more than about 15 parts by weight for each 100 parts by weight of cosmetic oil, although more can be used if desired.

It is preferred to employ formula (1) compounds in sunscreen compositions of the invention which are cosmetically acceptable from a color standpoint by which reference is had to the fact that the compounds of formula (1) which are employed in a given sunscreen composition are preferably white (colorless) or nearly white in color when in a substantially pure or bulk state. Examples of compounds within the scope of formula (1) which appear to be relatively highly colored include: N-4-methylphenylphthalisoimide, N-2-methoxyphenylphthalisoimide, N-4-methoxyphenylphthalisoimide, and the like. However, as those skilled in the art appreciate and as mentioned above, a dye can be added to a sunscreen composition to offset a cosmetically undesirable color associated with such a composition.

Sunscreen compositions of this invention are readily prepared by simply admixing selected compounds of formula (1) with cosmetic oils and by following the generally conventional cosmetic preparation procedures known to those skilled in the art. Elevated temperatures tend to promote, as desired, dissolution of the formula (1) in the cosmetic oils; for example, temperatures in the range of from about 25° to 105° degrees C. can be employed. Either prior to, or after, incorporation of the formula (1) compound(s) into a sunscreen composition, the various desired additives (such as above enumerated) can be added. Also, such additives could be concurrently added to a blend in the preparation procedure.

The sunscreen compositions of this invention are readily and conventionally employed by merely applying (spreading) the same upon exposed skin areas in order to achieve sunscreening action (ultra violet light radiation absorption). So far as is presently known, the N-phenylphthalisoimides of formula (1) in topical use on mammalian skin do not demonstrate any undesirable results.

The sunscreen compositions of this invention appear to provide the capacity for making highly effective (high UV absorbance) and highly economical broad spectrum ultra violet radiation absorbing systems.

Thermoset Polymeric Coatings

Paints, lacquers, varnishes, stains, and like coating compositions can be improved as regards UV absorbance characteristics by incorporating therewith at least one formula (1) compound in a dispersed and preferably completely dissolved state, thereby to produce coating formulations, which when applied and dried, result in thermoset polymeric coatings that have improved UV absorbance characteristics over prior art starting formulations containing no UV absorber. The result is that substrates with exposed surface portions coated with such coating compositions can be better protected against damage from UV radiation. Even the resulting thermoset polymeric coatings themselves have improved duty life characteristics owing to their better resistance to damage or degradation from UV radiation (by reason of the presence of formula (1) compounds therein).

For example, concentrations of from about 3 to 5%, based on solids, of formula (1) compounds can be dissolved or dispersed with stirring at room temperature in the following types of exemplary coating compositions:
(a) Two-component thermosetting urethane systems
(b) Epoxy coating systems
(c) Long-oil alkyd
(d) Thermosetting acrylic coatings
(e) Thermoplastic acrylic coatings Compounds of formulas (1) evidently do not react with metallic driers or promoters such as cobalt naphthenate and the like and such compounds have excellent compatibility at concentrations up to about 5%, based on total binder solids, in a wide range of coating systems.

Resin Blends

As is known by those skilled in the art, most polymers alone absorb very little UV radiation. However, impurities as well as chemicals added to the polymer system do absorb UV radiation and this is the starting point for UV degradation of a plastic product. To minimize the rate of degradation a compound of formula (1) is compoundable with a polymer system usually in an amount ranging from about 0.5 to 5 parts by weight per each 100 parts by weight of polymer. Conventional molding of the resulting polymer system results in increased outdoor life over products made with conventional prior art stabilizers. The broad spectrum absorbance characteristics makes the preferred compounds of formula (1) useful in resin blends.

The compatibility of formula (1) compounds with moldable polymers, together with their low volatility and good extraction resistance, indicates their suitability for use in rigid and flexible polyvinyl chloride, polyethylene, polypropylene (especially monofilament), acrylic polymers, such as polymethylmethacrylate, polyurethanes, polyacetates, polycarbonates, polyamides, styrene polymers, such as homopolystyrene, impact polystyrenes, ABS, polyesters, and the like.

It is convenient and presently preferred to use formula (1) compounds in polymers in combination with antioxidants. For example, 7 mil polypropylene monofilament containing (100 weight percent basis) 0.45 weight percent of the formula (1) compound identified as N-phenylphthalisoimide along with 0.2 weight percent Irganox 858 (available from Ciba Geigy) displays excellent stability and resistance to aqueous extraction (such as occurs in washing a fabric in a detergent solution).

Solid moldable polymers which are sensitive to UV radiation are improved as regards UV resistance by blending therewith at least one compound of formula (1).

For example, injection moldable resins are conveniently blended with formula (1) compound(s) by continuously admixing such formula (1) compound(s) with such resin in an extrude barrel wherein elevated temperatures and pressures are provided to assist in achieving a uniform distribution of formula (1) compound(s)

throughout the resin. Pelletizing and/or dicing of the extruded blend produces a particulate product of conventional form suitable for use as a molding resins or the like.

Concurrently with the admixing operation, various other additives can be compounded with the resin in the conventional manner thereby to incorporate dyes, pigments, plasticizers, lubricants, stabilizers, and the like with the resin, all as well known to those skilled in the art of molding resin manufacture.

A present preference is to employ from about 0.3 to 5 parts by weight of formula (1) compound(s) per each 100 parts by weight of molding resin, though larger and smaller quantities of formula (1) compound may be used. Strand pelletizing, die face cutting, underwater pelletizers, and the like can be employed. Where cut pellets are conveyed in a water slurry, the pellets are separated from the water and dried conveniently on sloping screens or in a centrifugal dryer.

The product resin blends are moldable in the conventional manner associated with the individual resins using the processing techniques well known to those skilled in the art. The fact that the product resin blends can be so conventionally molded is regarded as a distinct advantages and feature of this invention since otherwise new and previously untried molding procedures would be necessary which would be costly and time consuming from the user stand point. Thus, casting, injection molding, extrusion, blowing and related techniques can be employed. Product formed articles can be coated (by such procedures as extrusion coating, roll coating, and transfer coating), laminated, or the like.

EMBODIMENTS

The present invention is further illustrated by reference to the following examples. Those skilled in the art will appreciate that other and further embodiments are obvious and within the spirit and scope of this invention from the teachings of these present examples taken with the accompanying specification.

EXAMPLE 1

N-phenylphthalisoimide synthesis

Reactants:

| | 0.5 mole | the appropriate N—phenylphthalamic acid |
|---|---|---|
| 101 g | (1.0 mole) | triethylamine |
| 105 g | (0.5 mole) | trifluoroacetic anhydride |
| 600 ml | | dichloromethane |

Procedure:

The appropriate N-phenylphthalamic acid is placed in a 2 liter flask fitted with a thermometer, mechanical stirrer, and dropping funnel. The reaction is performed under a nitrogen atmosphere. The dichloromethane and triethylamine are charged to the reactor which is then cooled to 7 degrees C. in an ice bath. The trifluoroacetic anhydride is added dropwise over a 15 min. period with stirring. An exotherm to 14 degrees C. is observed. The stirrer is shut off, the ice bath removed, and the mixture is allowed to react for 16 hours. The solution is then washed with 2 liters of distilled water, dried over $MgSO_4$, and the solvent stripped under reduced pressure. 100 g (90% yield) of light yellow solid having a melting point of 112–115 degrees C. is collected which is believed to be N-phenylphthalisoimide. This material has the following UV characteristics:

| Ultraviolet Spectra Data Wavelength nm | Dichloromethane Solvent K Value |
|---|---|
| 300 | 27.5 |
| 327 | 36.8 |
| 350 | 27.3 |

EXAMPLES 2-12

Compound Synthesis

Using the procedure of Example 1, and replacing the appropriate N-phenylphthalamic acid with the individual starting material shown in Tables I and II below using equivalent molar proportion, there are produced the products shown in such Table I and identified as Examples 2-12.

TABLE I

EXAMPLES[1]

| Starting Material[2] | Product | Yield % | Melting Point Degrees C. | Wavelength (nm) | Dichloromethane Solvent K Value |
|---|---|---|---|---|---|
| 1. N—phenyl-phthalamic acid | N—phenyl phthalisoimide[3] | 90% | 112–115 C. | 300 | 27.5 |
| | | | | 327 | 36.8 |
| | | | | 350 | 27.3 |
| 2. N—4-chlorophenyl phthalamic acid | N—4-chlorophenyl[3] phthalisoimide | 63 | 143–147 | 350 | 28.3 |
| | | | | 333 | 34.4 |
| | | | | 300 | 20.2 |
| 3. N—3,4-dichlorophenyl phthalamic acid | N—3,4-dichlorophenyl[4] phthalisoimide | 58.6 | 195 | 350 | 11.5 |
| | | | | 330 | 14.4 |
| | | | | 300 | 14.4 |
| 4. N—4-methylphenyl phthalamic acid | N—4-methylphenyl[3] phthalisoimide | 60 | 86–91 | 370 | 17.0 |
| | | | | 347 | 31.6 |
| | | | | 300 | 19.4 |
| 5. N—2-methoxyphenyl phthalamic acid | N—2-methoxyphenyl[3] phthalisoimide | Not Calculated | 121.5–122.5 | 375 | 24.4 |
| | | | | 355 | 25.3 |
| | | | | 300 | 20.0 |
| 6. N—4-methoxyphenyl phthalamic acid | N—4-methoxyphenyl[3] phthalisoimide | 85 | 124–127 | 380 | 34.9 |
| | | | | 355 | 49.8 |
| | | | | 300 | 19.2 |
| 7. N—4-methoxyphenyl-4-methyl phthalamic acid | N—4-methoxyphenyl-4-[5] methyl phthalisoimide | 87 | 86–89 | 380 | 13.8 |
| | | | | 357 | 18.9 |
| | | | | 300 | 15.0 |

TABLE II

| Starting Material[2] | Product |
|---|---|
| 8. 4-bromophenyl phthalamic | 4-bromophenyl phthalisoimide |

TABLE II-continued

| Starting Material[2] | Product |
|---|---|
| acid | |
| 9. 4-iodophenyl phthalamic acid | 4-iodophenyl phthalisoimide |
| 10. 4-sulfophenyl phthalamic acid | 4-sulfophenyl phthalisoimide |
| 11. 4-octoxyphenyl phthalamic acid | 4-octoxyphenyl phthalisoimide |
| 12. 4-nitrophenyl phthalamic acid | 4-nitrophenyl phthalisoimide |

[1]The procedure described in Example 1 is used to synthesize all N—phenylphthalisoimides identified
[2]All starting N—phenylphthalamic acids are prepared according to the teachings of the article in J. Am. Chem. Soc. 94,8156 (1972)
[3]Product reported by Roderick, W. R., Parshotam, L. B. in J. Org. Chem. 28,2018 (1963)
[4]Product reported by Howe, K. H. in J. Org. Chem. 38,4164 (1973).
[5]Believed to be a new compound.

EXAMPLE 13

Sunscreen Composition

A sunscreen composition is prepared by dissolving 1 weight percent (total weight basis) of the N-phenylphthalisoimide prepared as described in Example 1 in isopropylmyristate as a cosmetic oil carrier. The resulting solution is found to have the following K values:

| Wavelength (nm) | K Value |
|---|---|
| 350 | 28.6 |
| 331 | 38.0 |
| 300 | 16.8 |

EXAMPLE 14

Sunscreen Composition

The procedure of Example 13 is repeated except that 2 weight percent of N-phenylphthalisoimide is so dissolved in the isopropylmyristate. The resulting solution is found to have the following K values:

| Wavelength (nm) | K Value |
|---|---|
| 350 | 27.8 |
| 331 | 38.9 |
| 305 | 24.8 |

EXAMPLE 15

Sunscreen Emulsion Formulas

Three experiments were run, to prepare emulsions of N-phenylphthalisoimide at concentrations of 2.0%, 5.0%, and 10.0%. These are designated as formulas I, II and III herein. These formulas are as follows:

| Materials | Weight Percent | | |
|---|---|---|---|
| | I | II | III |
| Part A | | | |
| N—phenylphthalisoimide (Ex. 1) | 2.00 | 5.00 | 10.00 |
| Isopropyl Myristate | 18.00 | 20.00 | 15.00 |
| Cosmetic Lanolin AA | 4.00 | 4.00 | 4.00 |
| Perfecta White Petrolatum | 2.00 | 2.00 | 2.00 |
| Glycerol Monostearate, Pure | 3.33 | 3.30 | 3.40 |
| P.E.G. 1000 Monostearate | 1.67 | 1.70 | 1.80 |
| Stearyl Alcohol | 2.00 | 2.00 | 2.00 |
| Propyl Paraben | 0.10 | 0.10 | 0.10 |
| Part B | | | |
| Methyl Paraben | 0.10 | 0.10 | 0.10 |
| Propylene Glycol | 4.00 | 4.00 | 4.00 |
| Distilled Water | 62.80 | 57.80 | 57.60 |

Procedure:

In formulas I and II, the N-phenylphthalisoimide is first dissolved in the isopropyl myristate, with heating as needed. Then the balance of the ingredients of Part A are needed. In a formula III melt of part A is dissolved the N-phenylphthalisoimide. In all three formulas, Parts A and B are initially separately heated to 80° C. and then add Part B to Part A with strong mixing followed by cooling with mixing down to a temperature of 35° C. Each batch is homogenized and packaged.

EXAMPLE 16

Coating System and Articles Coated Therewith

A thermosetting urethane clear liquid coating system based on Rohm & Haas AU-568 and Desmodur N-75 from Mobay and containing about 1.5 weight percent (based on total weight of dried coating binder solids) of N-phenylphthalisoimide as a UV absorber (UV stabilizer) is prepared and applied to an opaque test substrate.

The above procedure is repeated except that there is additionally incorporated into the system as a hindered amine (about 1.0 weight percent of Tinuvin 292 from Ciba-Geigy based on total weight of dried coating binder solids).

The above procedure using a system with no stabilizer absorber is also similarly applied.

The resulting coated substrates are exposed to UV radiation. After 5° South Florida Black Box Exposure for 6 months, the 20° gloss of the unmodified control is found to be less than that of the modified coatings, demonstrating that the N-phenylphthalisoimide is a UV absorber in such coatings.

EXAMPLE 17

Coated Transparent Substrates

Samples of window glass and lens blanks are coated with each of the systems of the preceding examples. Each of the so coated products is found to display reduced UV transmission relative to the untreated samples shown that N-phenylphthalisoimide improves the UV absorption of such articles.

EXAMPLE 18

Coating System and Articles Coated Therewith

The procedure of Example A is repeated except that the urethane system is replaced by a green marine epoxy coating similar results are observed as regards UV absorbance.

EXAMPLE 19

Coating System and Articles Coated Therewith

The procedure of Example A is repeated except that the urethane system is replaced by a silver metallic pigmented thermosetting acrylic non aqueous dispersion. Similar results are observed as regards UV absorbance.

EXAMPLE 20

Coating System and Articles Coated Therewith

The procedure of Example A is repeated except that the urethane system is replaced by a silver metallic pigmented thermoplastic acrylic lacquer. Similar results are observed as regards UV absorbance.

EXAMPLE 21

Coating System and Articles Coated Therewith

The procedure of Example A is repeated except that the urethane system is replaced by a silver metallic pigmented thermoset acrylic enamel. Similar results are observed as regards UV absorbance.

EXAMPLE 22

Treated Fabric

Swatchesl of fabric (cotton, wool, polyester, rayon) are dried with yellow, blue, red and green acid leveling dyes with presence of N-phenylphthalisoimides from 10% weight aqueous solutions warranted at pH 2.0 and containing both sodium sulfate (about 5%) and sulfuric acid (about 3%) at a liquor to goods weight ratio of about 60:1. After the fabric was immersed in the bath at 40° C. the temperature is raised to 80° C. over about 30 minutes and held at 80° C. for a further estimated 60 minutes. Untreated (with N-phenylphthalisoimide) swatches are also similarly dyed.

Thereafter, resulting fabric swatches are rinsed in fresh water at ambient conditions and are dried at ambient conditions.

One set of the resulting swatches which is untreated with N-phenylphthalisoimide is immersed with a 10 weight percent aqueous solution of N-phenylphthalisoimide at ambient conditions for about 2 hours and thereafter the so treated swatches are as dried at ambient conditions.

When the treated swatches and the untreated (control swatches are exposed to sunlight behind window glass for about 2000 hours, it is observed that dye fading is reduced by the presence of N-phenylphthalisoimide.

EXAMPLE 23

Moldable Resin Blends

To a stationary mixer are charged:
PVC previously formulated with stabilizers, lubricants, antioxidants and pigmentation, and
N-phenylphthalisoimide at the rate of 5 parts by weight per 100 parts by weight resin. Mixing is continued until uniformity of the resulting mixtures is obtained under low intensity mix action.

The procedure is successively repeated with each of similarly preformulated homopolystyrene and polymethylmethacrylates.

The product in each case is diced and then injection molded into test slabs. Untreated (based on starting resins) controls are similarly processed.

Exposure for about 2000 hours to sunlight of the test slabs indicates that the treated N-phenylphthalisoimide containing products display less colorfading, greater structural integrity, and less surface alteration.

Having now fully described the invention, it will be apparent to one of ordinary skill in the art that many changes and modifications can be made thereto without departing from the spirit or scope of the invention as set forth herein.

We claim:

1. A sunscreen composition comprising in combination
(A) at least one compound of the formula:

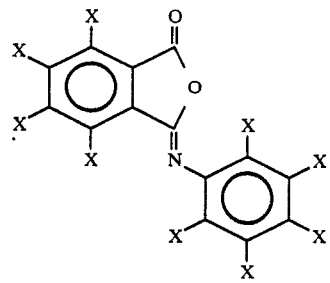

wherein:
each X is independently selected from the group consisting of hydrogen, —OR, —NR$_1$R$_2$, —Cl, —Br, —I, —NO$_2$, —C(O)OR, and hydrocarbyl,
R is selected from the group consisting of alkyl radicals and alkenyl radicals containing less than 11 carbon atoms each, and
R$_1$ and R$_2$ are each independently selected from the group consisting of hydrogen, alkyl radicals containing less than 11 carbon atoms each, and alkenyl radicals containing less than 11 carbon atoms each, and
(B) a cosmetic oil, said component (A) being dispersed in said component (B) in an effective sunscreening amount.

2. The composition of claim 1 wherein said component (A) is substantially completely dissolved in said component (B).

3. The composition of claim 1 wherein, for each 100 parts by weight of said component (B) then are from about 0.05 to 15 parts by weight of said component (A).

4. The composition of claim 1 wherein said cosmetic oil comprises a material selected from the group consisting of (a) esters of fatty acids with an alkanol containing between one and three hydroxyl groups per molecule and further containing less than 7 carbon atoms per molecule, (b) petroleum derived hydrocarbon oils and (c) silicone oils.

5. A sunscreen composition comprising
(A) at least one compound of the formula

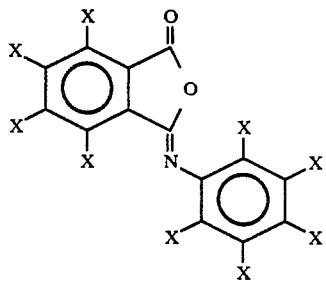

wherein:
each X is independently selected from the group consisting of hydrogen, —OR, —NR$_1$R$_2$, —Cl, —Br, —I, —NO$_2$, —C(O)OR, and hydrocarbyl,
R is selected from the group consisting of alkyl radicals and alkenyl radicals containing less than 11 carbon atoms each, and $R_1$ and $R_2$ are each independently selected from the group consisting of hydrogen, alkyl radicals containing less than 11 carbon atoms each, and alkenyl radicals containing less than 11 carbon atoms each, and (B) cosmetic oil, said component (A) being dissolved in said component (B) at the rate of from about 1.0 to 10 parts of said component (A) per each 100 parts by weight of said cosmetic oil.

6. An emulsion sunscreen composition comprising on a 100 weight percent basis:
(A) from about 0.5 to 25 weight percent of at least one compound of the formula (1)

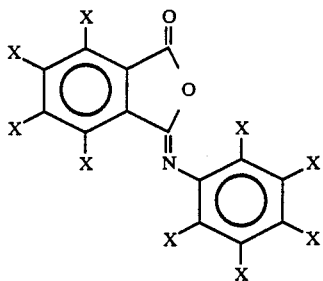

wherein:
each X is independently selected from the group consisting of hydrogen, —OR, —NR₁R₂, —Cl, —Br, —I, —NO₂, —C(O)OR, and hydrocarbyl, R is selected from the group consisting of alkyl radicals and alkenyl radicals containing less than 11 carbon atoms each, and $R_1$ and $R_2$ are each independently selected from the group consisting of hydrogen, alkyl radicals containing less than 11 carbon atoms each, and alkenyl radicals containing less than 11 carbon atoms each, (B) from about 5 to 98 weight percent water,
(C) from about 1 to 50 weight percent cosmetic oil which oil, when emulsified in such a sunscreen composition, exists in the form of droplets whose average diameter is less than about 500 millimicrons, and
(D) from 0 to about 15 weight percent of emulsifier, the amount of said emulsifier which is present in any given such sunscreen composition being at least sufficient to emulsify said cosmetic oil.

7. The sunscreen composition of claim 6 additionally containing from about 0.1 to 10 weight percent of a thickener.

8. The composition of claim 1 in which the N-phenylphthalisoimide is N-4-chlorophenylphthalisoimide.

9. The composition of claim 1 in which the N-phenylphthalisoimide is N-3,4-dichlorophenylphthalisoimide.

10. The composition of claim 1 in which the N-phenylphthalisoimide is N-4-methoxyphenyl-4-methylphthalisoimide.

11. The composition of claim 1 in which the N-phenylphthalisoimide consists of a mixture of N-phenylphthalisoimides.

12. The composition of claim 1 in which the N-phenylphthalisoimide is the compound N-phenylphthalisoimide.

13. A method of protecting the human skin from the effects of erythema and tanning radiation in sunlight which comprises applying to said skin a substituted N-phenylphthalisoimide contained in an effective sunscreening amount within a cosmetic oil carrier, said substituted N-phenylphthalisoimide having the formula:

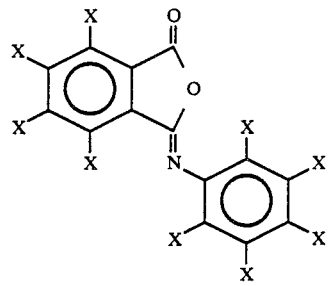

wherein:
each X is independently selected from the group consisting of hydrogen, —OR, —NR₁R₂, —Cl —Br, —I, —NO₂, —C(O)OR, and hydrocarbyl, R is selected from the group consisting of alkyl radicals and alkenyl radicals containing less than 11 carbon atoms each, and $R_1$ and $R_2$ are each independently selected from the group consisting of hydrogen, alkyl radicals containing less than 11 carbon atoms each and alkenyl radicals containing less than 11 carbon atoms each.

14. The method of claim 13 in which the N-phenylphthalisoimide is N-4-chlorophenylphthalisoimide.

15. The method of claim 13 in which the N-phenylphthalisoimide consists of a mixture of N-phenylphthalisoimides.

16. The method of claim 13 in which the N-phenylphthalisoimide is N-3,4-dichlorophenylphthalisoimide.

17. The method of claim 13 in which the N-phenylphthalisoimide is N-4-methoxyphenyl-4-methylphthalisoimide.

18. The method of claim 13 in which the N-phenylphthalisoimide is the compound N-phenylphthalisoimide.

19. A method of protecting the human skin from the effects of sunlight exhibiting broad spectra ultraviolet radiation which comprises applying to said skin a N-phenylphthalisoimide contained in a cosmetic oil carrier, the N-phenylphthalisoimide being distributed in said carrier in an effective amount to supply protection to the human skin, said N-phenyl-phthalisoimide having the formula:

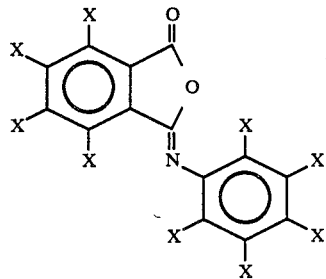

wherein:
each X is independently selected from the group consisting of hydrogen, —OR, —NR₁R₂, —Cl, —Br, —I, —NO₂, —C(O)OR, and hydrocarbyl, R is selected from the group consisting of alkyl radicals and alkenyl radicals containg less than 11 carbon atoms each, and $R_1$ and $R_2$ are each independently selected from the group consisting of hydrogen, alkyl radicals containing less than 11 carbon atoms each and alkenyl radicals containing less than 11 carbon atoms each.

* * * * *